United States Patent
Leonard et al.

(10) Patent No.: US 10,421,709 B1
(45) Date of Patent: Sep. 24, 2019

(54) BIPHASIC PRODUCTION OF 2,4,6-TRIAMINO-1,3,5-TRINITROBENZENE (TATB)

(71) Applicant: Triad National Security, LLC, Los Alamos, NM (US)

(72) Inventors: Philip Leonard, Los Alamos, NM (US); Michael Bange, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 16/398,612

(22) Filed: Apr. 30, 2019

(51) Int. Cl.
*C07C 209/10* (2006.01)
*C07C 211/52* (2006.01)

(52) U.S. Cl.
CPC .......... *C07C 209/10* (2013.01); *C07C 211/52* (2013.01)

(58) Field of Classification Search
CPC .... C07C 209/10; C07C 211/52; C07C 205/12
See application file for complete search history.

(56) References Cited

U.S. PATENT DOCUMENTS

| | | | |
|---|---|---|---|
| 4,032,377 A | 6/1977 | Benziger | |
| 4,481,371 A | 11/1984 | Benziger | |
| 4,952,733 A * | 8/1990 | Ott | C07C 209/10 564/406 |

* cited by examiner

*Primary Examiner* — Jafar F Parsa
(74) *Attorney, Agent, or Firm* — LeonardPatel PC; Michael Aristo Leonard, II; Sheetal Suresh Patel

(57) ABSTRACT

Production of 2,4,6-triamino-1,3,5-trinitrobenzene (TATB) through a safer, less harmful process while yielding a superior product is disclosed. The biphasic production process may include mixing a solution of 1,3,5-trichloro-2,4,6-trinitrobenzene (TCTNB) and a surfactant into a solvent in a sealed, heated vessel such that TATB is formed in a mixture. The biphasic production process may also include pressurizing the vessel with gaseous ammonia such that aqueous TATB is formed and separating the TATB from the mixture.

20 Claims, 5 Drawing Sheets

300

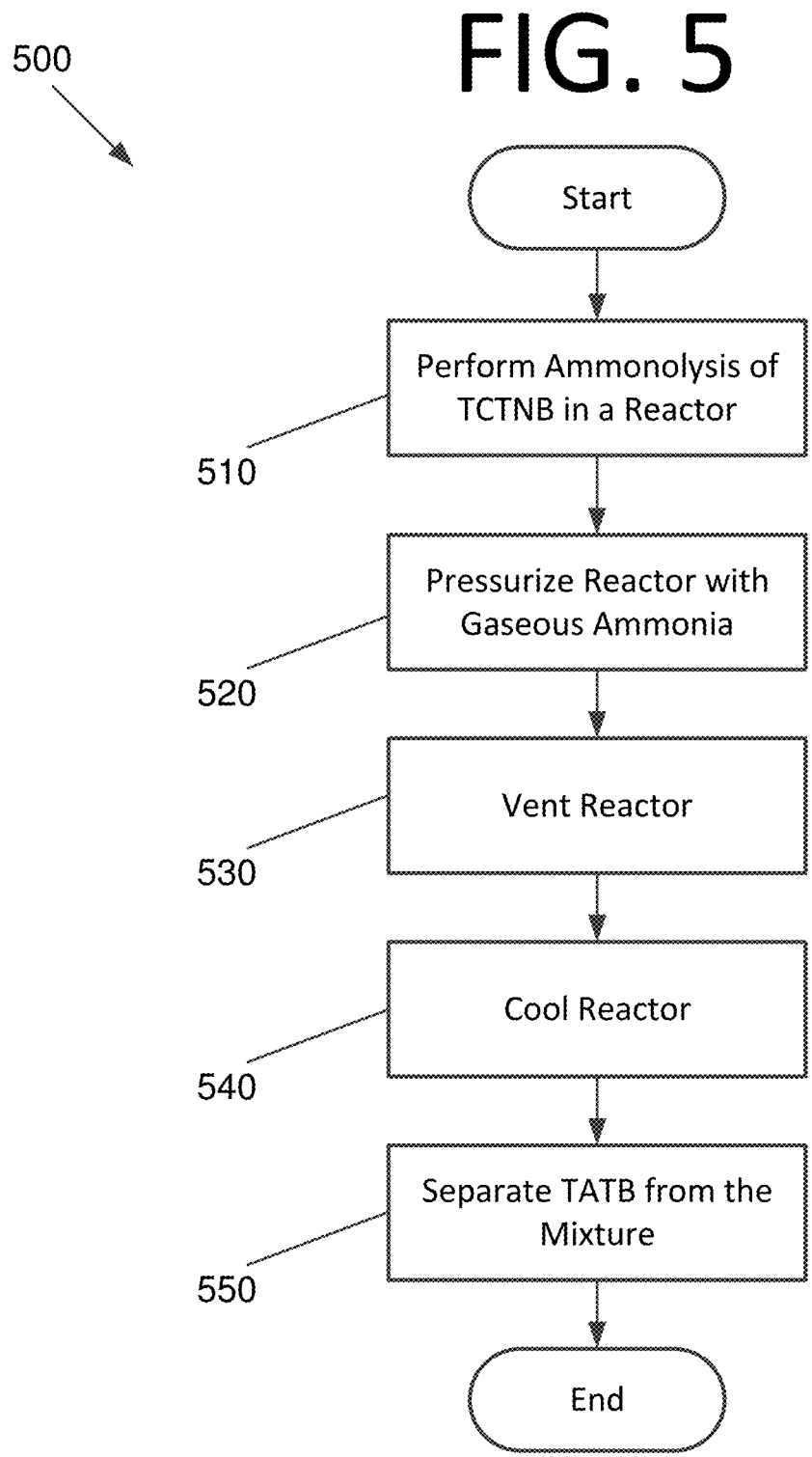

US 10,421,709 B1

BIPHASIC PRODUCTION OF 2,4,6-TRIAMINO-1,3,5-TRINITROBENZENE (TATB)

STATEMENT REGARDING FEDERAL RIGHTS

The United States government has rights in this invention pursuant to Contract No. 89233218CNA000001 between the United States Department of Energy and Triad National Security, LLC for the operation of Los Alamos National Laboratory.

FIELD

The present invention generally relates to the synthesis of insensitive high explosives, and more particularly, to the biphasic synthesis of TATB by ammonolysis of 1,3,5-trichloro-2,4,6-trinitrobenzene (TCTNB) using ammonia gas in a reactor.

BACKGROUND 2,4,6-triamino-1,3,5-trinitrobenzene (TATB) is a high explosive with exceptional properties in terms of thermal and physical stability, making it a safer alternative to many other high explosives, such as 2-methyl-1,3,5-trinitrobenzene (TNT). U.S. Pat. No. 4,032,377 discloses a widely practiced process for the manufacture of TATB, which is colloquially referred to as "The Benziger Process." This process uses the nitration of 1,3,5-trichloro-benzene to 1,3,5-trichloro-2,4,6-trinitrobenzene (TCTNB), which is then aminated to TATB using toluene as a solvent. Benziger went on to patent a process for making fine grained TATB in U.S. Pat. No. 4,481,371, where the reaction to produce TATB was conducted using an emulsion containing between approximately 50% and 75% water by volume, an emulsifier, and a protective colloid, with the remainder preferably consisting of toluene.

However, a safer TATB production process that produces higher yields while retaining and improving upon the desirable insensitivities, stabilities, and energetics of the explosive may be beneficial.

SUMMARY

Certain embodiments of the present invention may provide solutions to the problems and needs in the art that have not yet been fully identified, appreciated, or solved by conventional 2,4,6-triamino-1,3,5-trinitrobenzene (TATB) production processes. For example, some embodiments of the present invention pertain to processes for producing TATB that may include mixing a solution of 1,3,5-trichloro-2,4,6-trinitrobenzene (TCTNB) and a surfactant into a solvent in a sealed, heated vessel. The processes may also include pressurizing the vessel with gaseous ammonia such that a TATB mixture is formed and separating the TATB from the mixture.

In some embodiments, the solvent for the TCTNB is water. The pressure of the sealed vessel may be kept at or below 1 atmosphere (ATM) (i.e., 15 pounds per square inch gauge (PSIG)) and within the specifications and requirements of safe operation of the sealed pressure vessel. In certain embodiments, the temperature of the sealed pressure vessel is kept as high as possible while maintaining a pressure below 1 ATM (15 PSIG) in the sealed pressure vessel. Before the formed TATB is collected in from the mixture, the reactor vessel may be vented to reduce the pressure, and the reactor vessel and its contents may then be allowed to cool to approximately 60 degrees Celsius. In some embodiments, the TATB may then be separated from the mixture by filtration through a Buchner funnel with a cellulose filter, or separated on plate frame filter press using cellulose and/or nylon filters.

Benefits and advantages of some embodiments of the present invention include the efficient production of TATB at a production-relevant scale while increasing the safety of the production of TATB and using reagents with decreased toxicity and a less hazardous nature than conventional processes for the production of TATB. Some embodiments of the present invention have the benefit of producing TATB with a particle size distribution and morphology consistent with more favorable handling and thermal sensitivity. In some embodiments of the present invention, the reaction creates TATB that is instantly and effectively managed by ammonia pressure so that the reaction rate is controlled.

In an embodiment, a method for producing TATB includes performing ammonolysis of TCTNB by mixing ammonia gas with a solution of TCTNB, a solvent, and a surfactant in a reactor such that TATB is formed within a mixture. The method also includes separating the TATB from the mixture.

In another embodiment, a method for producing TATB includes performing ammonolysis of TCTNB by mixing ammonia gas with a solution of TCTNB, water, and a cosolvent surfactant in a reactor such that TATB is formed within a mixture. The method also includes separating the TATB from the mixture.

In yet another embodiment, a method for producing TATB includes performing ammonolysis of TCTNB by mixing ammonia gas with a solution of TCTNB, water, and a phase transfer catalyst in a reactor such that TATB is formed within a mixture. The method also includes separating the TATB from the mixture.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 5 is a flowchart illustrating a process for producing TATB, according to an embodiment of the present invention.

DETAILED DESCRIPTION OF THE EMBODIMENTS

Figure 1:
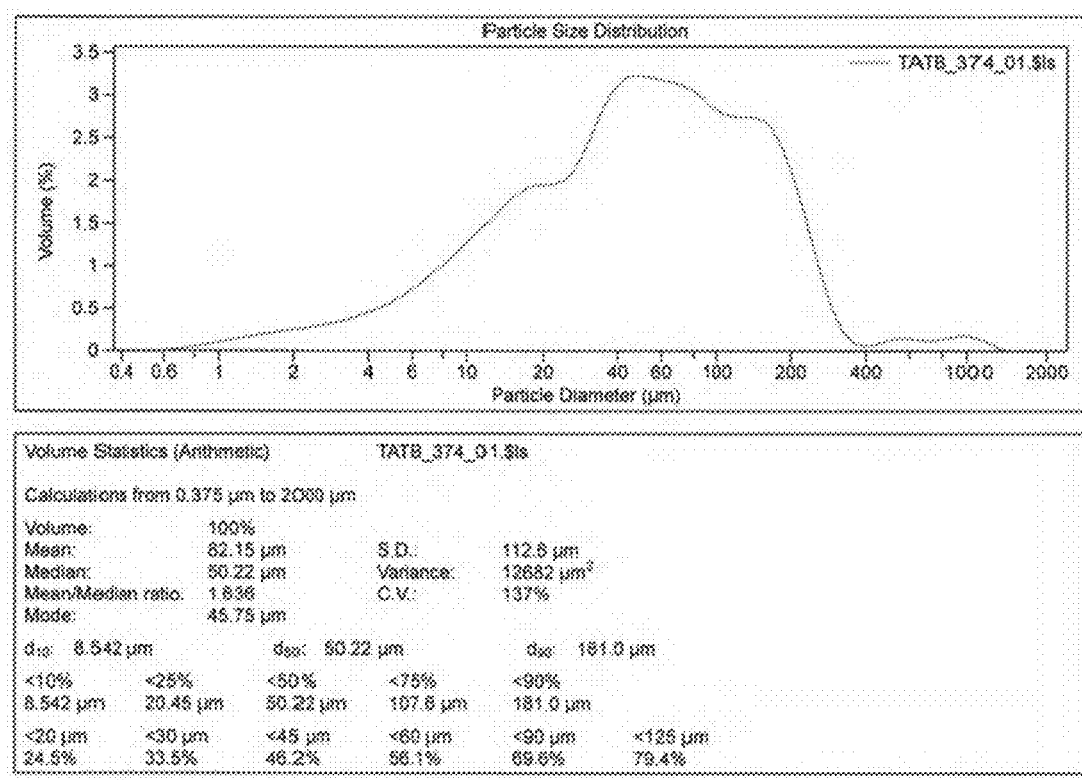
FIG. 1. is a graph of the volume percent and accompanying data of TATB produced by gaseous amination of TCTNB in water with t-butanol serving as a cosolvent surfactant as a function of particle diameter, according to an embodiment of the present invention. The graph also illustrates the particle size distribution for the produced TATB.

Some embodiments of the present invention pertain to the direct preparation of aqueous 2,4,6-triamino-1,3,5-trinitrobenzene (TATB) crystals by using gaseous ammonia for the ammonolysis of 1,3,5-trichloro-2,4,6-trinitrobenzene (TCTNB) in a solvent with a surfactant. These components may be mixed in a sealed, heated pressure vessel. The TATB may then be collected from suspension by filtration. Particle size analysis was performed for TATB produced via the process of some embodiments using a Coulter machine, which obtains data via laser refractometry methodology.

The sealed, heated pressure vessel is a reactor vessel capable of withstanding the temperatures and pressures of the process of the respective embodiment. In some embodiments, the reaction is conducted below 1 ATM (15 PSIG) and the sealed, heated pressure vessel. The sealed, heated pressure vessel is synonymously referred to herein as a reactor vessel or sealed pressure vessel, and includes, but is not limited to, commercial examples referred to as a Parr bomb or Pfaudler reactors, a glass-lined steel vessel, or any other suitable vessel without deviating from the scope of the invention. Suitable reactor vessels are capable of safe operation at the temperatures and pressures of the process of the respective embodiment for producing aqueous TATB.

In the process of some embodiments, TATB may be efficiently prepared in high purity and at production-relevant scale by performing the amination of TCTNB in water with gaseous ammonia and a surfactant. The water used in some embodiments need not be high purity, deionized, or distilled. However, such higher purity water may be used without deviating from the scope of the invention.

The function of using a surfactant, e.g., a phase transfer catalyst (PTC) or cosolvent surfactant, is to expose the TCTNB to the ammonia in the aqueous solution to allow for surfactant-mediated ammonolysis. Suitable cosolvent surfactants for some embodiments include, but are not limited to, such chemicals as cationic ammonium salts (e.g., benzyltriethylammonium chloride), an anionic surfactant (e.g., sodium, potassium, ammonium, salts of alkyl carboxylates, sodium dodecyl sulfate, aryl carboxylates, and/or ammonium toluene-sulfonate), etc. Further suitable cosolvent surfactants include, but are not limited to, miscible organic alcohols and/or miscible organic ethers (e.g., methanol, ethanol, 1-propanol, 2-propanol, t-butyl alcohol, and/or dimethoxyethane) etc.

In some embodiments, any quaternary ammonium salt, non-coordinating anionic salt, hindered organic alcohol, and/or ethylene glycol ether derivative may serve as a phase transfer catalyst (PTC). Additionally, suitable phase transfer catalysts in some embodiments can be a cationic ammonium salt, such as tetra-alkyl ammonium salts, aryl-trialkyl ammonium salts, other quaternary ammonium halides, carbonates, sulfates, and/or other ammonium salts with a non-nucleophilic ammonium cation (e.g., benzyltriethylammonium chloride).

The following examples provide processes that were used to produce TATB in some embodiments.

Example 1—Added Cosolvent Surfactant

Figure 2:
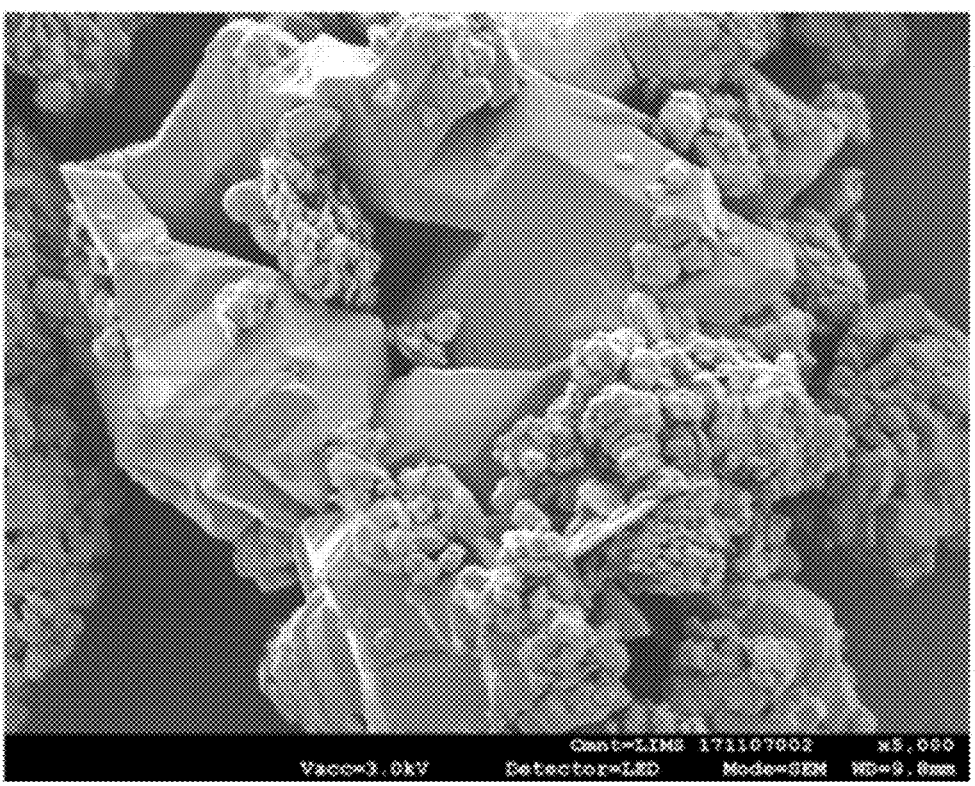
FIG. 2. is a scanning electron micrograph of TATB produced as in FIG. 1, according to an embodiment of the present invention.

A two-liter Parr bomb was charged with TCTNB (23.7 grams (g), 0.075 mol), 25 milliliters of t-butanol, and 225 milliliters of water. The reactor was sealed and heated to 95° C., at which point gaseous ammonia was added at a total pressure of 20 pounds per square inch (psi), an overpressure of 10 psi. The mixture was stirred for 2 hours at a rate of 325 rotations per minute (rpm) using a 6-bladed impeller. Pressure was vented and the reactor was cooled to 60° C. before the product was isolated on a 15-centimeter (cm) Buchner funnel with a cellulose filter. The product TATB (19.1 g, 0.074 mol) was recovered in 98% yield and 99% purity, with the balance being unreacted TCTNB. The particle size distribution and morphology can be found in graph 100 of FIG. 1 and scanning electron micrograph 200 of FIG. 2, respectively.

Example 2—Added Phase Transfer Catalyst

Figure 3:
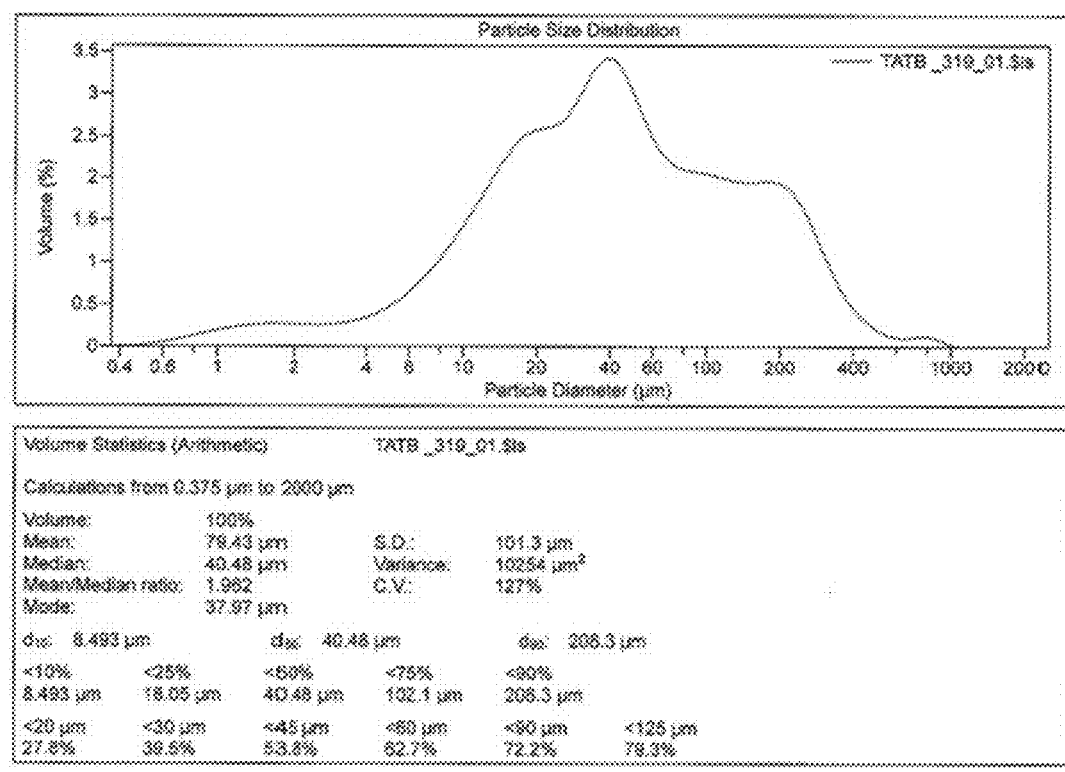
FIG. 3. is a graph of the volume percent and accompanying data of TATB produced by gaseous amination of TCTNB in water with benzyltriethylammonium chloride serving as a phase transfer catalyst, according to an embodiment of the present invention. The graph also illustrates the particle size distribution for the produced TATB.
Figure 4:
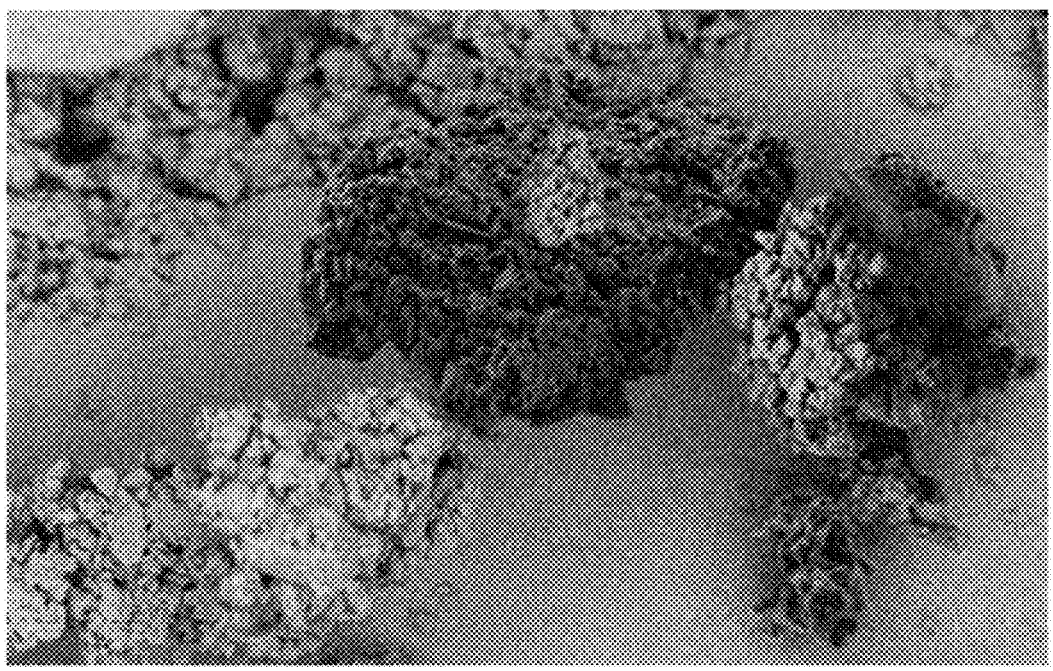
FIG. 4 is a scanning electron micrograph of TATB produced as in FIG. 3, according to an embodiment of the present invention.

A 30-gallon Pfaudler reactor was charged with TCTNB (1900 g, 6.01 mol), benzyltriethylammonium chloride (1.9 g, 0.008 mol), and 20 liters of process water. The reactor was sealed and heated to 99° C., at which point gaseous ammonia was added at a total pressure of 14 psi, an overpressure of about 10 psi. The mixture was stirred for 3 hours at a rate of 75 rpm using a 3-bladed impeller. Pressure was vented and the reactor was cooled to 60° C. before the product was isolated on a plate frame filter press using cellulose filters. The product TATB (1500 g, 5.8 mol) was recovered in 97% yield. The particle size distribution and particle morphology can be found in graph 300 of FIG. 3 and scanning electron micrograph 400 of FIG. 4, respectively.

FIG. 5 is a flowchart illustrating a process 500 for producing TATB, according to an embodiment of the present invention. The process begins with performing ammonolysis of TCTNB by mixing ammonia gas with a solution of TCTNB, a solvent, and a surfactant in a reactor at 510 such that TATB is formed within a mixture. The ammonolysis includes addition of gaseous ammonia at a sufficient temperature and pressure such that the TATB is formed at 520. The reactor is vented at 530 to reduce the pressure, and the reactor and its contents are cooled to approximately 60° C. at 540. The TATB is then separated from the mixture at 550.

In some embodiments, the solvent includes water. In certain embodiments, the reactor is a sealed, heated pressure vessel. In some embodiments, the surfactant includes a phase transfer catalyst. In certain embodiments, the phase transfer catalyst includes a cationic ammonium salt, which may be selected from the group consisting of tetra-alkyl ammonium salts, aryl-trialkyl ammonium salts, quaternary ammonium halides, quaternary ammonium carbonates, quaternary ammonium sulfates, and benzyltriethylammonium chloride.

In some embodiments, the surfactant includes a cosolvent surfactant, which may include an anionic surfactant, a cationic surfactant, a miscible organic alcohol, a miscible organic ether, or any combination thereof. In certain embodiments, the cosolvent surfactant includes an anionic surfactant, which may be sodium salts of alkyl carboxylates, potassium salts of alkyl carboxylates, ammonium salts of alkyl carboxylates, sodium dodecyl sulfate, and/or ammonium toluene-sulfonate. In some embodiments, the cosolvent surfactant includes a miscible organic alcohol, which may be methanol, ethanol, 1-propanol, 2-propanol, and/or t-butyl alcohol. In certain embodiments, the cosolvent surfactant includes a miscible organic ether, which may be dimethoxyethane, 1,2-dimethoxyethane, and/or 1,2-diethoxyethane.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A method for producing 2,4,6-triamino-1,3,5-trinitrobenzene (TATB), comprising:
performing ammonolysis of 1,3,5-trichloro-2,4,6-trinitrobenzene (TCTNB) by mixing ammonia gas with a solution of TCTNB, a solvent, and a surfactant in a reactor such that TATB is formed within a mixture; and
separating the TATB from the mixture.

2. The method of claim 1, wherein the solvent comprises water.

3. The method of claim 1, wherein the reactor comprises a sealed, heated pressure vessel.

4. The method of claim 1, wherein the ammonolysis comprises addition of gaseous ammonia at a sufficient temperature and pressure such that the TATB is formed.

5. The method of claim 4, further comprising:
venting the reactor to reduce the pressure from the gaseous ammonia.

6. The method of claim 5, further comprising:
cooling the reactor and the mixture, or allowing the reactor and the mixture to cool, to approximately 60° C.

7. The method of claim 1, wherein the surfactant comprises a phase transfer catalyst.

8. The method of claim 7, wherein the phase transfer catalyst comprises a cationic ammonium salt.

9. The method of claim 8, wherein the cationic ammonium salt is selected from the group consisting of tetra-alkyl ammonium salts, aryl-trialkyl ammonium salts, quaternary ammonium halides, quaternary ammonium carbonates, quaternary ammonium sulfates, and benzyltriethylammonium chloride.

10. The method of claim 1, wherein the surfactant comprises a cosolvent surfactant.

11. The method of claim 10, wherein the cosolvent surfactant comprises an anionic surfactant selected from the group consisting of sodium salts of alkyl carboxylates, potassium salts of alkyl carboxylates, ammonium salts of alkyl carboxylates, sodium dodecyl sulfate, and ammonium toluene-sulfonate.

12. The method of claim 10, wherein the cosolvent surfactant comprises a miscible organic alcohol selected from the group consisting of methanol, ethanol, 1-propanol, 2-propanol, and t-butyl alcohol.

13. The method of claim 10, wherein the cosolvent surfactant comprises a miscible organic ether selected from the group consisting of dimethoxyethane, 1,2-dimethoxyethane, and 1,2-diethoxyethane.

14. A method for producing 2,4,6-triamino-1,3,5-trinitrobenzene (TATB), comprising:
performing ammonolysis of 1,3,5-trichloro-2,4,6-trinitrobenzene (TCTNB) by mixing ammonia gas with a solution of TCTNB, water, and a cosolvent surfactant in a reactor such that TATB is formed within a mixture; and,
separating the TATB from the mixture.

15. The method of claim 14, wherein the cosolvent surfactant comprises an anionic surfactant, a cationic surfactant, a miscible organic alcohol, a miscible organic ether, or any combination thereof.

16. The method of claim 15, wherein the surfactant comprises an anionic surfactant selected from the group consisting of sodium salts of alkyl carboxylates, potassium salts of alkyl carboxylates, ammonium salts of alkyl carboxylates, sodium dodecyl sulfate, aryl carboxylates, and ammonium toluene-sulfonate.

17. The method of claim 15, wherein the cosolvent surfactant comprises a miscible organic alcohol selected from the group consisting of methanol, ethanol, 1-propanol, 2-propanol, and t-butyl alcohol.

18. The method of claim 15, where the cosolvent surfactant comprises the miscible organic ether, which comprises dimethoxyethane.

19. A method for producing 2,4,6-triamino-1,3,5-trinitrobenzene (TATB), comprising:
performing ammonolysis of 1,3,5-trichloro-2,4,6-trinitrobenzene (TCTNB) by mixing ammonia gas with a solution of TCTNB, water, and a phase transfer catalyst in a reactor such that TATB is formed within a mixture; and, separating the TATB from the mixture.

20. The method of claim 19, wherein the phase transfer catalyst is selected from the group consisting of tetra-alkyl ammonium salts, aryl-trialkyl ammonium salts, quaternary ammonium halides, quaternary ammonium carbonates, quaternary ammonium sulfates, and benzyltriethylammonium chloride.

* * * * *